United States Patent
Cockett et al.

(12)

(10) Patent No.: US 6,960,649 B2
(45) Date of Patent: Nov. 1, 2005

(54) HUMAN POTASSIUM CHANNEL POLYNUCLEOTIDES AND POLYPEPTIDES AND USES THEREOF

(75) Inventors: Mark Ian Cockett, Newtown, PA (US); Daniel Wayne Dilks, Marlton, NJ (US); Huai-Ping Chang Ling, Princeton Junction, NJ (US); Patricia Tyson Sokol, Bedminster, NJ (US)

(73) Assignee: Wyeth, Madison, NJ (US)

( * ) Notice: Subject to any disclaimer, the term of this patent is extended or adjusted under 35 U.S.C. 154(b) by 156 days.

(21) Appl. No.: 10/062,879

(22) Filed: Jan. 31, 2002

(65) Prior Publication Data

US 2002/0127649 A1 Sep. 12, 2002

Related U.S. Application Data

(62) Division of application No. 09/178,109, filed on Oct. 23, 1998, now Pat. No. 6,395,477.

(51) Int. Cl.[7] ................................................ C07K 1/00
(52) U.S. Cl. ..................................... 530/350; 435/69.1
(58) Field of Search .......................... 530/350; 435/69.1

(56) References Cited

U.S. PATENT DOCUMENTS 6,368,823 B1 * 4/2002 Bril et al. .................. 435/69.1

OTHER PUBLICATIONS

Dixon et al. Roel of the Kv4.3 K+ channel in ventricular muscle—A molecular correlate for the transient outward current. Circ Res. Oct., 1996, 79(4):659–68.*

Locus KCD3_RAT, and P70622, Dixon et al., Circ Res. 1996, 79(4):659–68 (sequence search results only).*

Serodio, E., et al., "Cloning of a Novel Component of A–Type K+ Channels Operating at Subthreshold Potentials with Unique Expression in Heart and Brain." *Journal of Neurophysiology*, 75(5):2174–2179 (1996).

Dixon, J., et al., "Role of the Kv4.3 K+ Channel in Ventricular Muscle," *Circulation Research*, 79(4): 659–668 (1996).

Dilks, O., et al., "Cloning and Expression of the Human Kv4.3 Potassium Channel," *Rapid Communication*, 1974–1977 (1998).

Ohya, S., et al., "Molecular Cloning and Tissue Distribution of an Alternatively Spliced Variant of an A–Type K+ Channel α–subunit, Kv4.3 in the Rat," *FEBS Letters*, 420: 47–53(1997).

Isbrandt, Dirk, et al., Gene Structures and Expression Profiles of Three Human KCND (Kv4) Potassium Channels Mediating A–Type Current $I_{TO}$ and $I_{SA}$, *Genomics* 64, Dec. 21, 1999, pp. 144–154.

* cited by examiner

Primary Examiner—Elizabeth Kemmerer
Assistant Examiner—Dong Jiang
(74) Attorney, Agent, or Firm—Nixon Peabody LLP; Raymond Van Dyke

(57) ABSTRACT

Novel human Kv4.3 polypeptides, polynucleotides which encode these polypeptides, and methods for producing these polypeptides are provided. Diagnostic, therapeutic, and screening methods employing the polynucleotides and polypeptides of the present invention are also provided.

8 Claims, 5 Drawing Sheets

SEQUENCE LISTING

<160> NUMBER OF SEQ ID NOS: 4

<210> SEQ ID NO 1
<211> LENGTH: 2121
<212> TYPE: DNA
<213> ORGANISM: human

<400> SEQUENCE: 1

```
gatttgctga actaactcca agctggtgtg cctagcgtcc gcgcggctgc cggcccaaga      60
gctggagtca ccatggcggc cggagttgcg gcctggctgc cttttgcccg ggctgcggcc     120
atcgggtgga tgccggtggc caactgcccc atgccctgg ccccggccga caagaacaag     180
cggcaggatg agctgattgt cctcaacgtg agtgggcgga ggttccagac ctggaggacc     240
acgctggagc gctacccgga caccctgctg ggcagcacgg agaaggagtt cttcttcaac     300
gaggacacca aggagtactt cttcgaccgg gaccccgagg tgttccgctg cgtgctcaac     360
ttctaccgca cggggaagct gcactacccg cgctacgagt gcatctctgc ctacgacgac     420
gagctggcct tctacggcat cctcccggag atcatcgggg actgctgcta cgaggagtac     480
aaggaccgca gagggagaa cgccgagcgg ctcatgacg acaacgactc ggagaacaac     540
caggagtcca tgccctcgct cagcttccgc cagaccatgt ggcgggcctt cgagaacccc     600
cacaccagca cgctggccct ggtcttctac tacgtgactg gcttcttcat cgctgtctcg     660
gtcatcacca acgtggtgga gacggtgccg tgcggcacgg tcccgggcag caaggagctg     720
ccgtgcgggg agcgctactc ggtggccttc ttctgcctgg acacggcgtg cgtcatgatc     780
ttcaccgtgg agtacctcct gcggctcttc gcggctccca gccgctaccg cttcatccgc     840
agcgtcatga gcatcatcga cgtggtggcc atcatgcct actacatcgg tctggtcatg     900
accaacaacg aggacgtgtc cggcgccttc gtcacgctcc gggtcttccg cgtcttcagg     960
atcttcaagt tttcccgcca ctcccagggc ctgcggatcc tgggctacac actgaagagc    1020
tgtgcctccg aactgggctt tcttctcttc tccctcacca tggccatcat catctttgcc    1080
actgtgatgt tttatgccga gaagggctcc tcggccagca gttcacaag catccctgcc    1140 tcgtttttggt acaccattgt caccatgacc acactgggat acgagacat ggtgcctaag    1200 acgattgcag ggaagatctt cggctccatc tgctccttga gtggcgtcct ggtcattgcc    1260
ctgccagtcc ctgtgattgt ttccaactttt agccggattt accaccagaa tcagagagct    1320
gataaacgca gggcacaaaa gaaggcccgc cttgccagga tccgtgtggc caaaacaggc    1380
agttcgaatg catacctgca cagcaagcgc aacgggctcc tcaacgaggc gctggagctg    1440
```

```
acgggcaccc cagaagagga gcacatgggc aagaccacct cactcatcga gagccagcat    1500
catcacctgc tgcactgcct ggaaaaaacc actgggttgt cctatcttgt ggatgatccc    1560
ctgttatctg tacgaacctc caccatcaag aaccacgagt ttattgatga gcagatgttt    1620
gagcagaact gcatggagag ttcaatgcag aactacccat ccacaagaag tccctcactg    1680
tccagccacc caggcctcac taccacctgc tgctcccgtc gtagtaagaa gaccacacac    1740
ctgcccaatt ctaacctgcc agctactcgc ctgcgcagca tgcaagagct cagcacgatc    1800
cacatccagg gcagtgagca gccctccctc acaaccagtc gctccagcct taatttgaaa    1860
gcagacgacg gactgagacc aaactgcaaa acatcccaga tcaccacagc catcatcagc    1920
atccccactc ccccagcgct aaccccagag ggggaaagtc ggccaccccc tgccagccca    1980
ggccccaaca cgaacattcc ttccataacc agcaatgttg tcaaggtctc tgtcttgtaa    2040
aaatcccgcg gccatggcgg ccgggagcat gcgacgtcgg gcccaattcg ccctatagtg    2100
agtcgtatta aagccgaatt c                                              2121
```

<210> SEQ ID NO 2
<211> LENGTH: 655
<212> TYPE: PRT
<213> ORGANISM: human

<400> SEQUENCE: 2

```
Met Ala Ala Gly Val Ala Ala Trp Leu Pro Phe Ala Arg Ala Ala
  1               5                  10                  15

Ile Gly Trp Met Pro Val Ala Asn Cys Pro Met Pro Leu Ala Pro Ala
                 20                  25                  30

Asp Lys Asn Lys Arg Gln Asp Glu Leu Ile Val Leu Asn Val Ser Gly
         35                  40                  45

Arg Arg Phe Gln Thr Trp Arg Thr Thr Leu Glu Arg Tyr Pro Asp Thr
     50                  55                  60

Leu Leu Gly Ser Thr Glu Lys Glu Phe Phe Phe Asn Glu Asp Thr Lys
 65                  70                  75                  80

Glu Tyr Phe Phe Asp Arg Asp Pro Glu Val Phe Arg Cys Val Leu Asn
                 85                  90                  95

Phe Tyr Arg Thr Gly Lys Leu His Tyr Pro Arg Tyr Glu Cys Ile Ser
                100                 105                 110

Ala Tyr Asp Asp Glu Leu Ala Phe Tyr Gly Ile Leu Pro Glu Ile Ile
            115                 120                 125

Gly Asp Cys Cys Tyr Glu Glu Tyr Lys Asp Arg Lys Arg Glu Asn Ala
        130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
            180                 185                 190

Ile Ala Val Ser Val Ile Thr Asn Val Val Glu Thr Val Pro Cys Gly
        195                 200                 205

Thr Val Pro Gly Ser Lys Glu Leu Pro Cys Gly Glu Arg Tyr Ser Val
    210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
```

-continued

```
                245                 250                 255
Ser Val Met Ser Ile Ile Asp Val Val Ala Ile Met Pro Tyr Tyr Ile
            260                 265                 270
Gly Leu Val Met Thr Asn Asn Glu Asp Val Ser Gly Ala Phe Val Thr
            275                 280                 285
Leu Arg Val Phe Arg Val Phe Arg Ile Phe Lys Phe Ser Arg His Ser
        290                 295                 300
Gln Gly Leu Arg Ile Leu Gly Tyr Thr Leu Lys Ser Cys Ala Ser Glu
305                 310                 315                 320
Leu Gly Phe Leu Leu Phe Ser Leu Thr Met Ala Ile Ile Phe Ala
                325                 330                 335
Thr Val Met Phe Tyr Ala Glu Lys Gly Ser Ser Ala Ser Lys Phe Thr
            340                 345                 350
Ser Ile Pro Ala Ser Phe Trp Tyr Thr Ile Val Thr Met Thr Thr Leu
            355                 360                 365
Gly Tyr Gly Asp Met Val Pro Lys Thr Ile Ala Gly Lys Ile Phe Gly
        370                 375                 380
Ser Ile Cys Ser Leu Ser Gly Val Leu Val Ile Ala Leu Pro Val Pro
385                 390                 395                 400
Val Ile Val Ser Asn Phe Ser Arg Ile Tyr His Gln Asn Gln Arg Ala
                405                 410                 415
Asp Lys Arg Arg Ala Gln Lys Lys Ala Arg Leu Ala Arg Ile Arg Val
            420                 425                 430
Ala Lys Thr Gly Ser Ser Asn Ala Tyr Leu His Ser Lys Arg Asn Gly
        435                 440                 445
Leu Leu Asn Glu Ala Leu Glu Leu Thr Gly Thr Pro Glu Glu Glu His
    450                 455                 460
Met Gly Lys Thr Thr Ser Leu Ile Glu Ser Gln His His His Leu Leu
465                 470                 475                 480
His Cys Leu Glu Lys Thr Thr Gly Leu Ser Tyr Leu Val Asp Asp Pro
                485                 490                 495
Leu Leu Ser Val Arg Thr Ser Thr Ile Lys Asn His Glu Phe Ile Asp
            500                 505                 510
Glu Gln Met Phe Glu Gln Asn Cys Met Glu Ser Ser Met Gln Asn Tyr
        515                 520                 525
Pro Ser Thr Arg Ser Pro Ser Leu Ser Ser His Pro Gly Leu Thr Thr
    530                 535                 540
Thr Cys Cys Ser Arg Arg Ser Lys Lys Thr Thr His Leu Pro Asn Ser
545                 550                 555                 560
Asn Leu Pro Ala Thr Arg Leu Arg Ser Met Gln Glu Leu Ser Thr Ile
                565                 570                 575
His Ile Gln Gly Ser Glu Gln Pro Ser Leu Thr Thr Ser Arg Ser Ser
            580                 585                 590
Leu Asn Leu Lys Ala Asp Asp Gly Leu Arg Pro Asn Cys Lys Thr Ser
        595                 600                 605
Gln Ile Thr Thr Ala Ile Ile Ser Ile Pro Thr Pro Pro Ala Leu Thr
    610                 615                 620
Pro Glu Gly Glu Ser Arg Pro Pro Ala Ser Pro Gly Pro Asn Thr
625                 630                 635                 640
Asn Ile Pro Ser Ile Thr Ser Asn Val Val Lys Val Ser Val Leu
                645                 650                 655
```

<210> SEQ ID NO 3

```
<211> LENGTH: 2064
<212> TYPE: DNA
<213> ORGANISM: human

<400> SEQUENCE: 3
gatttgctga actaactcca agctggtgtg cctagcgtcc gcgcggctgc cggcccaaga      60
gctggagtca ccatggcggc cggagttgcg gcctggctgc cttttgcccg ggctgcggcc     120
atcgggtgga tgccggtggc caactgcccc atgcccctgg ccccggccga caagaacaag     180
cggcaggatg agctgattgt cctcaacgtg agtgggcgga ggttccagac ctggaggacc     240
acgctggagc gctaccccga cccctgctg gcagcacgg agaaggagtt cttcttcaac       300
gaggacacca aggagtactt cttcgaccgg accccgagg tgttccgctg cgtgctcaac      360
ttctaccgca cggggaagct gcactacccg cgctacgagt gcatctctgc ctacgacgac     420
gagctggcct tctacggcat cctcccggag atcatcgggg actgctgcta cgaggagtac     480
aaggaccgca gagggagaa cgccgagcgg ctcatggacg caacgactc ggagaacaac      540
caggagtcca tgccctcgct cagcttccgc cagaccatgt ggcgggcctt cgagaacccc     600
cacaccagca cgctgccct ggtcttctac tacgtgactg gcttcttcat cgctgtctcg     660
gtcatcacca cgtggtgga cggtgccg tgcggcacgg tcccgggcag caaggagctg        720
ccgtgcgggg agcgctactc ggtggccttc ttctgcctgg acacgcgtg cgtcatgatc     780
ttcaccgtgg agtacctcct gcggctcttc gcggctccca gccgctaccg cttcatccgc     840
agcgtcatga gcatcatcga cgtggtggcc atcatgccct actacatcgg tctggtcatg     900
accaacaacg aggacgtgtc cggcgccttc gtcacgctcc gggtcttccg cgtcttcagg     960
atcttcaagt tttcccgcca ctcccagggc ctgcggatcc tgggctacac actgaagagc    1020
tgtgcctccg aactgggctt tcttctcttc tccctcacca tggccatcat catctttgcc    1080
actgtgatgt tttatgccga aagggctcc tcggccagca agttcacaag catccctgcc    1140
tcgttttggt acaccattgt caccatgacc acactgggat acggagacat ggtgcctaag    1200
acgattgcag ggaagatctt cggctccatc tgctccttga gtggcgtcct ggtcattgcc    1260
ctgccagtcc ctgtgattgt ttccaacttt agccggattt accaccagaa tcagagagct    1320
gataaacgca gggcacaaaa gaaggcccgc cttgccagga tccgtgtggc caaaacaggc    1380
agttcgaatg catacctgca cagcaagcgc aacgggctcc tcaacgaggc gctggagctg    1440
acgggcaccc cagaagagga gcacatgggc aagaccacct cactcatcga gagccagcat    1500
catcacctgc tgcactgcct ggaaaaaacc actaaccacg agtttattga tgagcagatg    1560
tttgagcaga actgcatgga gagttcaatg cagaactacc catccacaag aagtccctca    1620
ctgtccagcc acccaggcct cactaccacc tgctgctccc gtcgtagtaa gaagaccaca    1680
cacctgccca ttctaacct gccagctact cgcctgcgca gcatgcaaga gctcagcacg    1740
atccacatcc agggcagtga gcagcccccc ctcacaacca gtcgctccag ccttaatttg    1800
aaagcagacg acggactgag accaaactgc aaaacatccc agatcaccac agccatcatc    1860
agcatcccca ctcccccagc gctaacccca gaggggaaa gtcggccacc ccctgccagc    1920
ccaggcccca acacgaacat tccttccata accagcaatg ttgtcaaggt ctctgtcttg    1980
taaaaatccc gcggccatgg cggccggag catgcgacgt cgggcccaat tcgccctata     2040
gtgagtcgta ttaaagccga attc                                            2064

<210> SEQ ID NO 4
<211> LENGTH: 636
```

-continued

```
<212> TYPE: PRT
<213> ORGANISM: human

<400> SEQUENCE: 4

Met Ala Gly Val Ala Ala Trp Leu Pro Phe Ala Arg Ala Ala Ala
 1               5                  10                  15

Ile Gly Trp Met Pro Val Ala Asn Cys Pro Met Pro Leu Ala Pro Ala
                20                  25                  30

Asp Lys Asn Lys Arg Gln Asp Glu Leu Ile Val Leu Asn Val Ser Gly
                35                  40                  45

Arg Arg Phe Gln Thr Trp Arg Thr Thr Leu Glu Arg Tyr Pro Asp Thr
    50                  55                  60

Leu Leu Gly Ser Thr Glu Lys Glu Phe Phe Asn Glu Asp Thr Lys
65                  70                  75                  80

Glu Tyr Phe Phe Asp Arg Asp Pro Glu Val Phe Arg Cys Val Leu Asn
                        85                  90                  95

Phe Tyr Arg Thr Gly Lys Leu His Tyr Pro Arg Tyr Glu Cys Ile Ser
                100                 105                 110

Ala Tyr Asp Asp Glu Leu Ala Phe Tyr Gly Ile Leu Pro Glu Ile Ile
                115                 120                 125

Gly Asp Cys Cys Tyr Glu Glu Tyr Lys Asp Arg Lys Arg Glu Asn Ala
130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
                180                 185                 190

Ile Ala Val Ser Val Ile Thr Asn Val Val Glu Thr Val Pro Cys Gly
                195                 200                 205

Thr Val Pro Gly Ser Lys Glu Leu Pro Cys Gly Glu Arg Tyr Ser Val
                210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
                260                 265                 270

Gly Leu Val Met Thr Asn Asn Glu Asp Val Ser Gly Ala Phe Val Thr
                275                 280                 285

Leu Arg Val Phe Arg Val Phe Arg Ile Phe Lys Phe Ser Arg His Ser
                290                 295                 300

Gln Gly Leu Arg Ile Leu Gly Tyr Thr Leu Lys Ser Cys Ala Ser Glu
305                 310                 315                 320

Leu Gly Phe Leu Leu Phe Ser Leu Thr Met Ala Ile Ile Phe Ala
                325                 330                 335

Thr Val Met Phe Tyr Ala Glu Lys Gly Ser Ser Ala Ser Lys Phe Thr
                340                 345                 350

Ser Ile Pro Ala Ser Phe Trp Tyr Thr Ile Val Thr Met Thr Thr Leu
                355                 360                 365

Gly Tyr Gly Asp Met Val Pro Lys Thr Ile Ala Gly Lys Ile Phe Gly
                370                 375                 380

Ser Ile Cys Ser Leu Ser Gly Val Leu Val Ile Ala Leu Pro Val Pro
385                 390                 395                 400
```

-continued

```
Val Ile Val Ser Asn Phe Ser Arg Ile Tyr His Gln Asn Gln Arg Ala
            405                 410                 415

Asp Lys Arg Arg Ala Gln Lys Lys Ala Arg Leu Ala Arg Ile Arg Val
            420                 425                 430

Ala Lys Thr Gly Ser Ser Asn Ala Tyr Leu His Ser Lys Arg Asn Gly
            435                 440                 445

Leu Leu Asn Glu Ala Leu Glu Leu Thr Gly Thr Pro Glu Glu Glu His
        450                 455                 460

Met Gly Lys Thr Thr Ser Leu Ile Glu Ser Gln His His Leu Leu
465                 470                 475                 480

His Cys Leu Glu Lys Thr Thr Asn His Glu Phe Ile Asp Glu Gln Met
            485                 490                 495

Phe Glu Gln Asn Cys Met Glu Ser Ser Met Gln Asn Tyr Pro Ser Thr
            500                 505                 510

Arg Ser Pro Ser Leu Ser Ser His Pro Gly Leu Thr Thr Thr Cys Cys
            515                 520                 525

Ser Arg Arg Ser Lys Lys Thr Thr His Leu Pro Asn Ser Asn Leu Pro
        530                 535                 540

Ala Thr Arg Leu Arg Ser Met Gln Glu Leu Ser Thr Ile His Ile Gln
545                 550                 555                 560

Gly Ser Glu Gln Pro Ser Leu Thr Thr Ser Arg Ser Ser Leu Asn Leu
            565                 570                 575

Lys Ala Asp Asp Gly Leu Arg Pro Asn Cys Lys Thr Ser Gln Ile Thr
            580                 585                 590

Thr Ala Ile Ile Ser Ile Pro Thr Pro Pro Ala Leu Thr Pro Glu Gly
        595                 600                 605

Glu Ser Arg Pro Pro Ala Ser Pro Gly Pro Asn Thr Asn Ile Pro
            610                 615                 620

Ser Ile Thr Ser Asn Val Val Lys Val Ser Val Leu
625                 630                 635
```

HUMAN POTASSIUM CHANNEL POLYNUCLEOTIDES AND POLYPEPTIDES AND USES THEREOF

The present application is a division of U.S. patent application Ser. No. 09/178,109, filed Oct. 23, 1998, now U.S. Pat. No. 6,395,477.

FIELD OF THE INVENTION

The present invention relates to novel polynucleotides and proteins encoded by such polynucleotides, along with therapeutic, diagnostic, and research utilities for these polynucleotides and proteins. In particular, the present invention relates to the identification of a novel human voltage-gated potassium channel polynucleotide, Kv4.3, and isoforms thereof, polypeptides encoded by them, and their uses.

BACKGROUND OF THE INVENTION

Mammalian cell membranes are important to the structural integrity and activity of many cells and tissues. Of particular interest in membrane physiology is the study of trans-membrane ion channels which act to directly control a variety of pharmacological, physiological, and cellular processes. Numerous ion channels have been identified including calcium, sodium, and potassium channels, each of which has been investigated to determine their roles in vertebrate and insect cells.

Because of its involvement in maintaining normal cellular homeostasis, much attention has been given to potassium channels. A number of these potassium channels open in response to changes in the cell membrane potential. Many voltage-gated potassium channels have been identified are characterized by their electrophysiological and pharmacological properties. Potassium currents are more diverse than sodium or calcium currents and are further involved in determining the response of a cell to external stimulus. The diversity of potassium channels and their important physiological role highlights their potential as targets for developing therapeutic agents for various diseases.

One of the best characterized classes of potassium channels are the voltage-gated potassium channels. The prototypical member of this class is the protein encoded by the Shaker gene in *Drosophila melanogaster*. In addition to Shaker, three other classes of potassium channels. Shap, Shaw, and Shal have been identified in *Drosophila* Proteins of the Shal or the mammalian Kv4 family are a type of voltage-gated potassium channels that underlies many of the native A type currents that have been recorded from different primary cells (Serodio et al. 1994, 1998; Dixon et al. 1996). The Kv4 channel has a major role in the repolarization of cardiac atrial action potentials (Dixon et al. 1996). In neurons, Kv4 channels and the A currents they may comprise play an important role in modulation of firing rate, action potential initiation and in shaping burst pattern (Byrne 1980; Connor and Stevens 1971; Getting 1983; Hille 1992; Llinas 1988; McCormick and Huguenard 1992; Rudy 1988; Thompson and Aldrich 1980). Recently, A currents were localized to dendritic regions in the hippocampus where they play a complex role in modulating synaptic input and retrograde propagation of action potentials (Hoffman et al. 1997).

The gene encoding rat Kv4.3 channels have been cloned and expressed by several labs (Dixon et al. 1996; Serodio et al. 1996; Ohya et al. 1997 and Takimoto et al. 1997). The identification of the Kv4 family as the molecular correlate for the transient outward potassium current (also called the A current) in both heart and brain comes primarily from data obtained with *Xenopus* oocytes expressing rat Kv4 cloned channels. As in native neurons and myocytes, Kv4 channels display fast and complete inactivation at positive potentials. Initially however, the voltage dependency for steady-state activation and inactivation of these expressed Kv4 channels appeared to be shifted 20 mV positive to that seen in neurons, which would place them out of the subthreshold category. In addition the recovery from inactivation of the expressed channels was slower than that seen in the native cells. Fortunately it was discovered that addition of a low molecular weight RNA fraction from rat brain, presumably containing a beta subunit for the Kv4 channel, shifted the voltage dependence and speeds the channels rate of recovery from inactivation to that seen in the native cells (Serodio et al. 1994, 1996 and Chabala et al. 1993). Further confirmation of the role of Kv4 channels in forming A type currents comes from antisense hybrid-arrest and dominant-negative experiments in both neurons and cardiac myocytes (Johns et al. 1997; Fiset et al. 1997; Nakamura et al. 1997).

Until the present invention, the gene encoding human Kv4.3 had not been identified. The art needs molecular characterization of the human Kv4.3 channel in order to elucidate their function and properties in preventing or treating dysfunctions and diseases.

SUMMARY OF THE INVENTION

This invention provides novel isolated polynucleotides which encode human Kv4.3 potassium channel polypeptides. The polynucleotides of the present invention are isolated from human brain and heart and further comprise (a) polynucleotide comprising the potassium channel Kv4.3 nucleotide sequence set forth in SEQ. ID NO. 1 or in SEQ. ID NO. 3; (b) a polynucleotide having at least 90% identity over its entire length to a polynucleotide encoding a potassium channel Kv4.3 polypeptide of SEQ ID NO: 2 or SEQ ID NO: 4; (c) a polynucleotide which is an allelic variant of the polynucleotide of (a)–(b) above; and (d) a polynucleotide capable of hybridizing under stringent conditions to any one of the polynucleotides specified in (a)–(c).

Preferably such polynucleotides comprise the nucleotide sequence of SEQ ID NO: 1 or SEQ ID NO: 3.

In other embodiments, the present invention provides a composition comprising a Kv4.3 polypeptide, wherein said polypeptide comprises (a) an amino acid sequence which is at least 95% identical to the amino acid sequence of SEQ ID NO: 2 or SEQ ID NO: 4.

Preferably such polypeptides comprise the amino acid sequence of SEQ ID NO: 2 or SEQ ID NO: 4.

In certain preferred embodiments, the Kv4.3 polynucleotide is operably linked to an expression control sequence. The invention also provides a host cell, including bacterial, yeast, insect, amphibian and mammalian cells, transformed with such polynucleotides compositions.

Processes are also provided for producing Kv4.3 polypeptides.

Compositions comprising an antibody which specifically reacts with the polypeptide are also provided by the present invention.

Methods and diagnostic processes are provided for detecting a disease state characterized by aberrant expression of Kv4.3 polypeptides, as well as methods for identifying compounds which regulate the activity or expression of the polypeptides.

Another embodiment of the invention includes transgenic animals comprising a polynucleotide encoding a human Kv4.3 polynucleotide operably linked to an expression control sequence.

DETAILED DESCRIPTION OF THE INVENTION

Figure 1A:
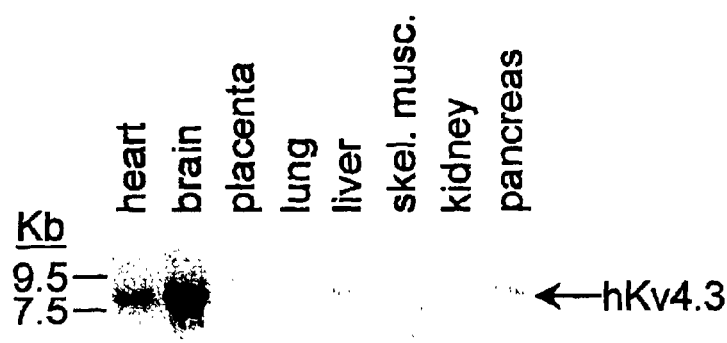
FIG. 1A. Human Multi-Tissue Northern blot, probed with human Kv4.3.

The present invention relates to the isolation and cloning of two isoforms of human Kv4.3. One form is full length (hereinafter "hKv4.3 long"), the second form has a deletion of 19 amino acids in the carboxy domain after the predicted sixth transmembrane domain (hereinafter "hKv4.3 short"). Both forms of hKv4.3 show high homology to the two rat forms that have been previously cloned with only a three amino acid difference. This high degree of amino acid conservation suggests that the Kv4.3 channel is evolutionarily highly conserved. The long and short forms of the channel are expressed in the human brain but that only the long form is found in the heart. These findings support the premise that the polynucleotides and polypeptides of the present invention may be used in the diagnosis, treatment, and screening of human diseases relating to either an excess or deficiency of hKv4.3 polypeptide activity, including but not limited to diseases such as Alzheimer's and heart disease.

Definitions

The terms "hKv4.3 proteins", "hKv4.3 peptides" and "hKv4.3 polypeptides" are used interchangeably and are intended to include the amino acid sequences set forth in SEQ ID NO: 2 or SEQ ID NO: 4 or purified and recombinantly produced molecules containing amino acids linearly coupled through peptide bonds. The amino acids of this invention can be in the L or D form so long as the biological activity of the polypeptide is maintained. For example, the protein can be altered so as to be secreted from the cell for recombinant production and purification. The proteins of this invention also include proteins that are post-translationally modified by reactions that include glycosylation, acetylation and phosphorylation. The hKv4.3 polypeptides also include analogs, alleles and allelic variants that can contain amino acid derivatives or non-amino acid moieties that do not affect the biological or functional activity of the protein as compared to wild-type or naturally occurring human protein. The term amino acid refers both to the naturally occurring amino acids and their derivatives, such as TyrMe and PheCl, as well as other moieties characterized by the presence of both an available carboxyl group and an amine group. Non-amino acid moieties that can be contained in such polypeptides include, for example, amino acid mimicking structures. Mimicking structures are those structures that exhibit substantially the same spatial arrangement of functional groups as amino acids but do not necessarily have both the amino and carboxyl groups characteristic of amino acids.

"Muteins" are proteins or polypeptides that have minor changes in amino acid sequence caused, for example, by site-specific mutagenesis or other manipulations; by errors in transcription or translation; or which are prepared synthetically by rational design. These minor alterations result in amino acid sequences wherein the biological activity of the protein or polypeptide is altered as compared to wild-type or naturally occurring Kv4.3 polypeptide or protein.

"Purified" when referring to a protein or polypeptide, is distinguishable from native or naturally occurring proteins or polypeptides because they exist in a purified state. These "purified" proteins or polypeptides, or any of the intended variations as described herein, shall mean that the compound or molecule is substantially free of contaminants normally associated with the compound in its native or natural environment. The terms "substantially pure" and "isolated" are not intended to exclude mixtures of polynucleotides or polypeptides with substances that are not associated with the polynucleotides or polypeptides in nature.

"Native" polypeptides, proteins, or nucleic acid molecules refer to those recovered from a source occurring in nature or "wild-type", such as in SEQ ID NO: 2 or SEQ ID NO: 4.

"Compound" is intended to mean small molecule chemical compounds as well as naturally occurring or synthetic peptides or polypeptides and other natural products, including but not limited to toxins.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see *Martin, Remington's Pharm. Sci., 15th Ed.* (Mack Publ. Co., Easton (1975)).

A "hKv4.3 polynucleotide" refers to the nucleic acid sequence set forth in SEQ ID NO: 1 or SEQ ID NO: 3. The term "nucleic acid" means single and double stranded DNA, cDNA, genome-derived DNA, and RNA, as well as the positive and negative strand of the nucleic acid that are complements of each other, including anti-sense RNA. A "nucleic acid molecule" is a term used interchangeably with "polynucleotide" and each refers to a polymeric form of nucleotides of any length, either ribonucleotides or deoxyribonucleotides, or analogs thereof. It also includes known types of modifications, for example labels which are known in the art (e.g., Sambrook et al. (1989) infra.), methylation, "caps", substitution of one or more of the naturally occurring nucleotides with an analog, internucleotide modifications such as, for example, those with uncharged linkages (e.g., methyl carbamate, etc.), those containing pendant moieties, such as for example, proteins (including, e.g., nuclease, toxins, antibodies, signal peptides, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. The polynucleotide can be chemically or biochemically modified or contain non-natural or derivatized nucleotide bases. The nucleotides may be complementary to the mRNA encoding the polypeptides. These complementary nucleotides include, but are not limited to, nucleotides capable of forming triple helices and antisense nucleotides. Recombinant polynucleotides comprising sequences otherwise not naturally occurring are also provided by this invention, as are alterations of wild-type polypeptide sequences, including but not limited to, those due to deletion, insertion, substitution of one or more nucleotides or by fusion to other polynucleotide sequences.

A polynucleotide is said to "encode" a polypeptide if, in its native state or when manipulated by methods well-known to those skilled in the art, it can be transcribed and/or translated to produce a polypeptide or mature protein. Thus, the term polynucleotide shall include, in addition to coding sequences, processing sequences and other sequences that do not code for amino acids of the mature protein. The anti-sense strand of such a polynucleotide is also said to encode the sequence.

An "analog" of DNA, RNA or a polynucleotide, refers to a macromolecule resembling naturally occurring polynucleotides in form and/or function (particularly in the ability to engage in sequence-specific hydrogen bonding to base pairs on a complementary polynucleotide sequence) but which differs from DNA or RNA in, for example, the possession of an unusual or non-natural base or an altered backbone. See for example, Uhlmann et al. (1990) *Chemical Reviews* 90:543–584.

"Isolated when referring to a nucleic acid molecule, means separated from other cellular components normally associated with native or wild-type DNA or RNA intracellularly.

"Hybridization" refers to hybridization reactions that can be performed under conditions of different "stringency". Conditions that increase the stringency of a hybridization reaction are widely known and published in the art: see, for example, Sambrook et al. infra. Examples of relevant conditions include (in order of increasing stringency): incubation temperatures of 25° C., 37° .C, 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%, incubation times from 5 minutes to 24 hours and washes of increasing duration, increasing frequency, or decreasing buffer concentrations.

A "sense" strand and an "antisense" strand when used in the same context refer to single-stranded polynucleotides which are complementary to each other. They may be opposing strands of a double-stranded polynucleotide, or one strand may be predicted from the other according to generally accepted base-pairing rules. Unless otherwise specified or implied, the assignment of one or the other strand as "sense" or "antisense" is arbitrary.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotide, the sequence for the DNA reflects the order of nitrogenous bases in the polydeoxyribonucleotide, and the two sequences satisfy the other requirements of this definition. Where at least one of the sequences is a degenerate oligonucleotide comprising an ambiguous residue, the two sequences are identical if at least one of the alternative forms of the degenerate oligonucleotide is identical to the sequence with which it is being compared. For example, AYAAA is identical to ATAAA, if AYAAA is a mixture of ATAAA and ACAAA.

A linear sequence of nucleotides is "essentially identical" or the "equivalent" to another linear sequence, if both sequences are capable of hybridizing to form duplexes with the same complementary polynucleotide. It should be understood, although not always explicitly stated that Applicants refer to a specific nucleic acid molecule, its equivalents are also intended. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. Sequences that correspond or align more closely to the invention disclosed herein are comparably more preferred. Generally, a polynucleotide region of about 25 residues is essentially identical to another region, if the sequences are at least about 80% identical; more preferably, they are at least about 90% identical; more preferably, they are at least about 95% identical; still more preferably, the sequences are 100% identical. A polynucleotide region of 40 residues or more will be essentially identical to another region, after alignment of homologous portions if the sequences are at least about 75% identical; more preferably, they are at least about 80% identical; more preferably, they are at least about 85% identical; even more preferably, they are at least about 90% identical; still more preferably, the sequences are 100% identical.

In determining whether polynucleotide sequences are essentially identical, a sequence that preserves the functionality of the polynucleotide with which it is being compared is particularly preferred. Functionality can be determined by different parameters. For example, if the polynucleotide is to be used in reactions that involve hybridizing with another polynucleotide, then preferred sequences are those which hybridize tot he same target under similar conditions. In another example, if the polypeptide encoded by the polynucleotide is an important part of its functionality, then preferred sequences are those which encode identical or essentially identical polypeptides. Thus, nucleotide differences which cause a conservative amino acid substitution are preferred over those which can cause a non-conservative amino acid substitution are preferred over those which cause a non-conservative substitution, nucleotide differences which do not alter the amino acid sequence are more preferred, while identical nucleotides are even more preferred. Insertions or deletions in the polynucleotide that result in insertions or deletions in the polypeptide are preferred over those that result in the down-stream coding regions being rendered out of phase; polynucleotide sequences comprising no insertions or deletions are even more preferred. The relative importance of hybridization properties and the encoded polypeptide sequence of a polynucleotide depends on the application of the invention.

A polynucleotide has the same characteristics or is the equivalent of another polynucleotide if both are capable of forming a stable duplex with a particular third polynucleotide under similar conditions of maximal stringency. Preferably, in addition to similar hybridization properties, the polynucleotides also encode essentially identical polypeptides.

"Conserved" residues of a polynucleotide sequence are those residues which occur unaltered in the same position of two or more related sequences being compared. Residues that are relatively conserved are those that are conserved amongst more related sequences than residues appearing elsewhere in the sequences.

As used herein, a "degenerate" oligonucleotide sequence is a designed sequence derived from at least two related originating polynucleotide sequences as follows: the residues that are conserved in the originating sequences are preserved in the degenerate sequence, while residues that are not conserved in the originating sequences may be provided as several alternatives in the degenerate sequence. For example, the degenerate sequence AYASA may be assigned from originating sequences ATACA and ACAGA, where Y is C or T and S is C or G. Y and S are examples of "ambiguous" residues. A degenerate segment is a segment of a polynucleotide containing a degenerate sequence.

A polynucleotide "fragment" or "insert" or "deletion" as used herein generally represents a sub-region of the full-length form, but the entire full-length polynucleotide may also be included.

Different polynucleotides "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides also "correspond" to each other if they serve a similar function, such as encoding a related polypeptide, in different species, strains or variants that are being compared.

As used herein, the term "operatively linked" means that the DNA molecule is positioned relative to the necessary regulation sequences, e.g., a promoter or enhancer, such that the promoter will direct transcription of RNA off the DNA molecule in a stable or transient manner.

"Vector" means a self-replicating nucleic acid molecule that transfers an inserted nucleic acid molecule into and/or between host cells. The term is intended to include vectors that function primarily for the replication of nucleic acid and expression vectors that function for transcription and/or translation of the DNA or RNA. Also intended are vectors that provide more than one of the above functions "Host cell" is intended to include any individual cell or cell culture that can be or have been recipients for vectors or the incorporation of exogenous nucleic acid molecules and/ or proteins. It also is intended to include progeny of a single cell, and the progeny may not necessarily be completely identical (in morphology or in genomic or total DNA complement) to the original parent cell due to natural, accidental, or deliberate mutation.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody (as defined above) and its binding partner or ligand.

A "suitable cell" for the purposes of this invention is one that includes but is not limited to a cell expressing human Kv4.3 e.g., an amphibian cell, such as Xenopus, a bone marrow cell, an endothelial cell, a breast carcinoma cell, a fibroblast cell, an epithelial cell, an epithelial tumor cell (see Spriggs, D. R. et al. (1988) J. Clin. Inves. 81:455–460), a T cell (TCR+, CD8+ or CD4+ T cells), a peripheral blood lymphocyte, leukocyte, and mixed leukocyte cultures (MLC), a B-lymphoma cell (ATCC, A202J), a colon cell, a small intestine cell, an ovarian cell, a testis cell, a prostate cell, a thymic cell, a spleen cell, a kidney cell, a liver cell, a lung cell, a brain cell and monocytes.

A "biological equivalent" of a nucleic acid molecule is defined herein as one possessing essential identity with the reference nucleic acid molecule. A fragment of the reference nucleic acid molecule is one example of a biological equivalent.

The hKv4.3 Coding Sequence

In accordance with the present invention, nucleotide sequences which encode hKv4.3, fragments, fusion proteins or functional equivalents thereof, may be used to generate recombinant DNA molecules that direct the expression of hKv4.3, or a functionally active peptide, in appropriate host cells. Alternatively, nucleotide sequences which hybridize to portions of the hKv4.3 sequence may be used in nucleic acid hybridization assays, Southern and Northern blot assays, etc.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein.

The complete amino acid sequence of hKv4.3 long with the insert region highlighted, is aligned with rat Kv4.3 (Imaizumi et al. 1997), rat Kv4.2 (Baldwin et al. 1991), and mouse Kv4.1 (Pak et al. 1991). When compared to the previously reported rat clones of Kv4.3 (Rudy et al., McKinnon, and Imaizumi), the two variants of the hKv4.3 clones are 91% homologous at the nucleotide level and differ by only three amino acids.

Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3–6.4, incorporated herein by reference.

Preferably, each such hybridizing polynucleotide has a length that is at least 25%(more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

Expression of hKv4.3 hKv4.3 was expressed in *Xenopus* oocytes by injecting RNA encoding Kv4.3 into the oocyte. The isolated polynucleotides of the invention may also be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian, lower eukaryotes such as yeast or prokaryotes such as bacteria, insect, and amphibian cells are suitable expression systems.

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl7 or Cibacrom blue 3GA Sepharose7; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The Kv4.3 proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of Kv4.3 proteins which would be expected to retain protein activity in whole or in part and may thus be useful for screening or other immunological methodologies may also be easily made by those skilled in the art given the disclosures herein. Such modifications are believed to be encompassed by the present invention.

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologues of the disclosed polynucleotides and proteins are also provided by the present invention. As used herein, a species homologue is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75% identity; most preferably at least 90% identity) with the given polynucleotide, and protein species homologues have at least 30% sequence identity (more preferably, at least 45% identity; most preferably at least 60% identity) with the given protein, where sequence identity is determined by comparing the nucleotide sequences of the polynucleotides or the amino acid sequences of the proteins when aligned so as to maximize overlap and identity while minimizing sequence gaps. Species homologues may be isolated and identified by making suitable probes or primers from the sequences provided herein and screening a suitable nucleic acid source from the desired species. Preferably, species homologues are those isolated from mammalian species. Most preferably, species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Mus musculus, Rattus norvegicus, Cricetulus griseus, Felis catus, Mustela vison, Canis familiaris, Oryctolagus cuniculus, Bos taurus, Ovis aries, Sus scrofa,* and *Equus caballus,* for which genetic maps have been created allowing the identification of syntenic relationships between the genomic organization of genes in one species and the genomic organization of the related genes in another species (O'Brien and Seuanez, 1988, Ann. Rev. Genet. 22: 323–351; O'Brien et al., 1993, Nature Genetics 3:103–112; Johansson et al., 1995, Genomics 25: 682–690; Lyons et al., 1997, Nature Genetics 15: 47–56; O'Brien et al., 1997, Trends in Genetics 13(10): 393–399; Carver and Stubbs, 1997, Genome Research 7:1123–1137; all of which are incorporated by reference herein).

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75% identity; most preferably at least 90% identity) with the given polynucleotide, where sequence identity is determined by comparing the nucleotide sequences of the polynucleotides when aligned so as to maximize overlap and identity while minimizing sequence gaps. Allelic variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

EXAMPLES

The present invention is further described by the following examples. The examples are provided solely to illustrate the invention by reference to specific embodiments. These exemplifications, while illustrating certain specific aspects of the invention do not portray the limitations or circumscribe the scope of the invention.

Example 1

Cloning of hKv4.3 Long Isoform

To obtain hKv4.3 cDNA, oligonucleotides were synthesized based on the published rat sequence (Rudy et. al., GenBank U42975). Four overlapping partial cDNA fragments were pulled out of a whole heart cDNA library (Gibco BRL). A 511 bp fragment was used as a probe to rescreen the same library, but the resulting clones still lacked the extreme 5' and 3' coding regions. Therefore, rapid amplification of cDNA ends (5' and 3' RACE) was used to amplify these sequences from a human brainstem cDNA library (Stratagene).

Example 2

Cloning of hKv4.3 Short Isoform

In rat, evidence of two isoforms of Kv4.3 differing by a +/−57 base pair insert. In order to see if a shorter form of hKv4.3 existed in human tissue we synthesized primers that flanked the 57 bp insert in the long form of hKv4.3. These generated products of either 237 bp or 180 bp, reflecting the presence or absence of the 57 bp insertion. Both forms were identified in human brain (FIG. 1C). To clone the shorter version a second set of flanking primers were synthesized and used to generate two bands (767 bp and 710 bp). The shorter band was cloned and sequenced to confirm the absence of the 57 bp region. BglII and SacI sites flank this region and were used with the 710 bp product to directionally clone the shorter fragment of hKv4.3 into the corresponding region of full length hKv4.3.

Example 3

Tissue Distribution of hKv4.3

A human multiple tissue (heart, brain, placenta, lung, liver, skeletal muscle, kidney, and pancreas) northern (MTN) blot was purchased from Clontech. A set of primers (forward GCC TAA GAC AAT TGC TGG GA, reverse GGT GCG TGG TCT TCT TGC TAC), which flanked the deleted region, were used to amplify a fragment to be used as a probe. The probe was $^{32}P$ labeled by using Promega's Prime-a-Gene labeling system. The final probe concentration was $2\times10^6$ cpm/ml.

Figure 1B:
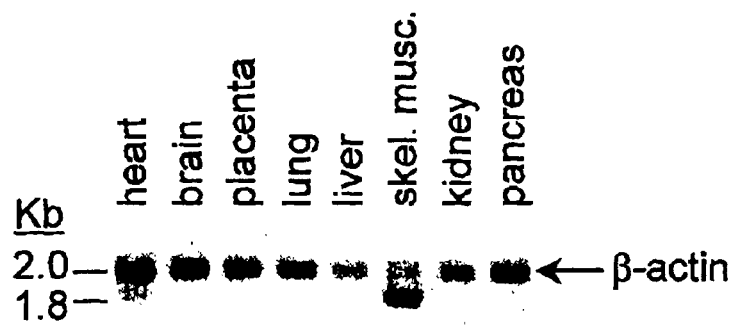
FIG. 1B. Human Multi-Tissue Northern blot, probed with b-actin control.
Figure 1C:
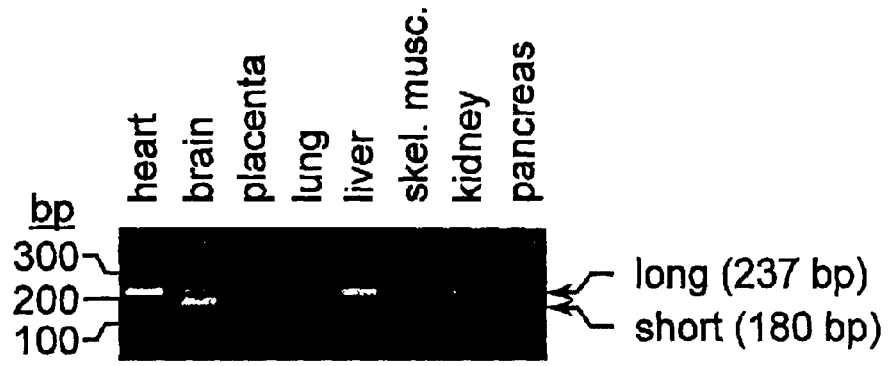
FIG. 1C. RT-PCR showing tissue distribution of hKv4.3 splice variants (of short and long forms) for the corresponding tissue set.

FIG. 1B shows the tissue northern blot and RT-PCR for both hKv4.3 short and hKv4.3 long. Human heart primarily expresses hKv4.3 long whereas human brain can be seen to contain both forms.

Example 4

Electrophysiological Characterization of hKv4.3 Isoforms hKv4.3 was cloned into a Bluescript KSM vector at HindIII and EcoRI sites. The vector was kindly provided by Dr. Bill Joiner, Yale University. cRNA was generated by using Ambion's mMessage mMachine in vitro transcription kit. A 0.9 $\mu$g/$\mu$l cRNA stock was stored at −70° C. Diluted aliquots were later used for *Xenopus* Oocyte injection.

Figure 2A:
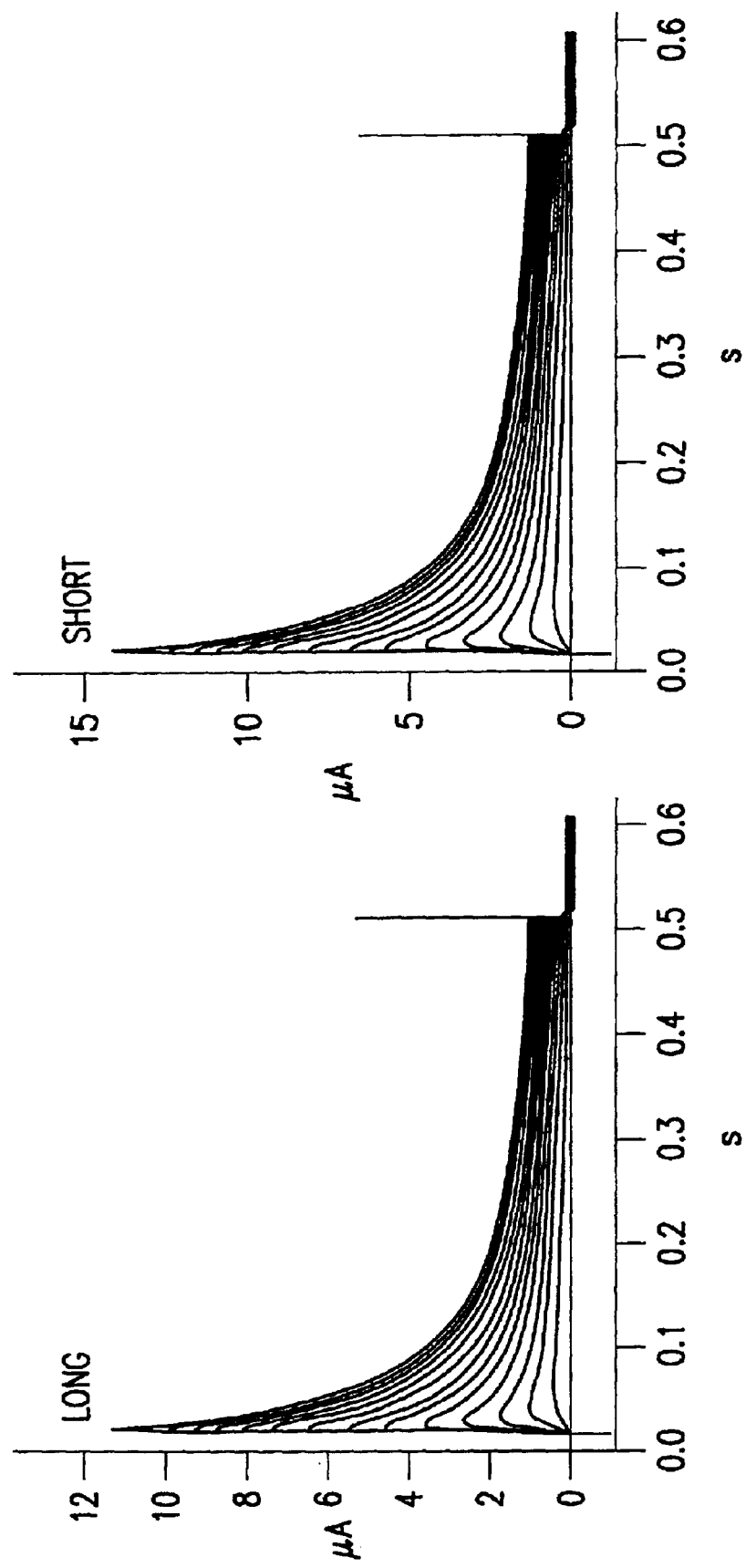
FIG. 2A. Raw current traces from both short and long forms of hKv4.3 expressed in *Xenopus* oocytes in response to voltage steps from −60 to +80 mV in 10 mV 500 ms steps, holding potential=−80 mV.
Figure 2B:
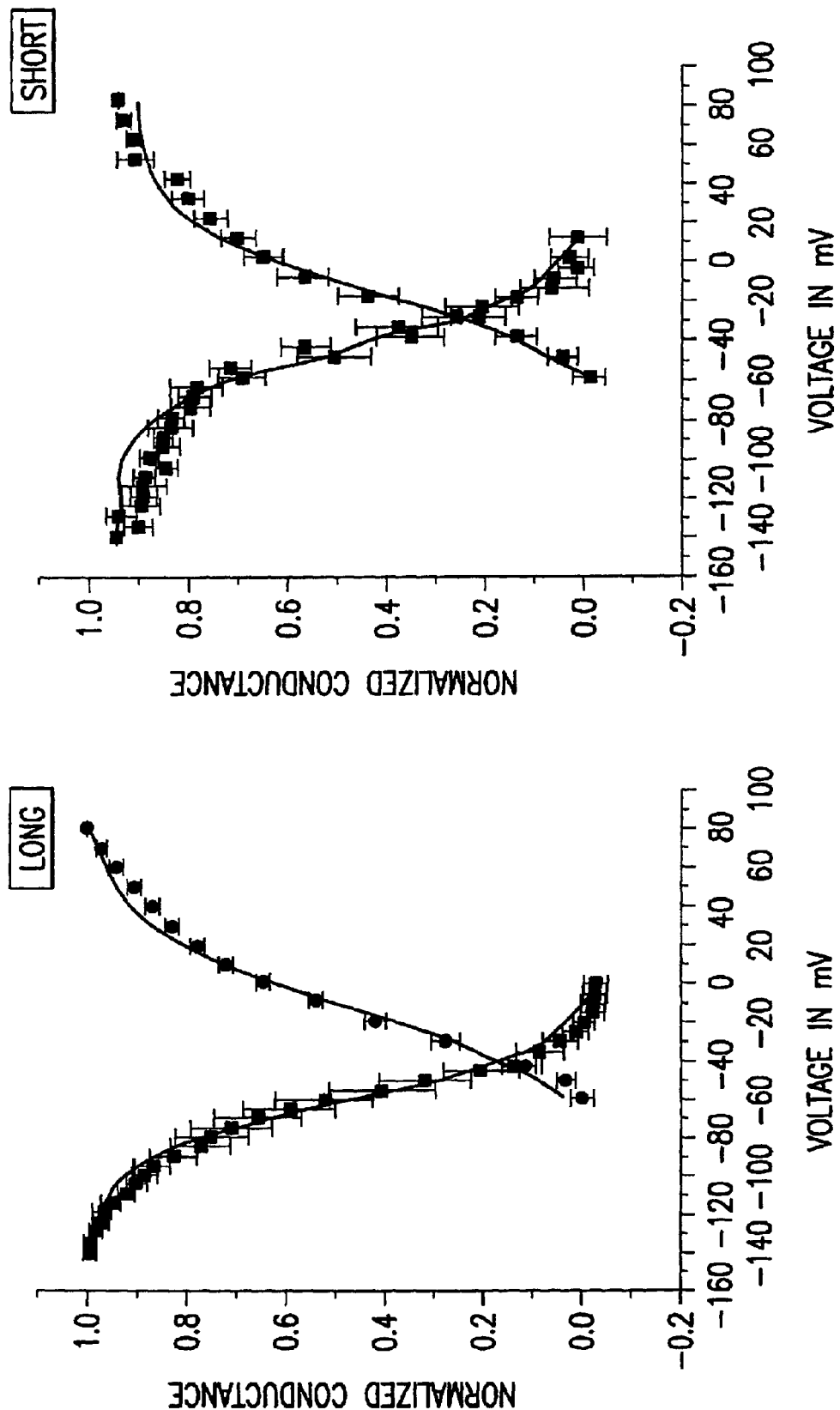
FIG. 2B. Average plots of normalized steady-state inactivation and steady-state activation of conductance for both short and long forms of hKv4.3.

FIG. 2A shows raw current traces from depolarizing voltage pulses for hKv4.3 long and hKv4.3 short expressed in *Xenopus* oocytes. The inactivation of the current during the pulse was largely voltage independent (−25 to +80 mV) and was well fitted by two exponentials with time constants of 20±2.2 and 120±5.8 ms for hKv4.3 long and 22±3.2 and 125±4.1 ms for hKv4.3 short (n=12). There were no significant difference in the kinetics of the currents between the two forms. FIG. 2B shows the steady-state activation and inactivation curves for both forms of hKv4.3 expressed in *Xenopus* oocytes. The Boltzman fits of the steady-state inactivation curves for the short and long form of hKv4.3 reveal that the V1/2 of inactivation is shifted 11 mV positive for the hKv4.3 short relative to the hKv4.3 long (see FIG. 2 legend). Activation was also seen to shift by 5 mV positive for hKv4.3 short relative to hKv4.3long. The overlap region for the steady-state activation and inactivation of both forms of the channel shows a prominent window current with a relative peak amplitude of 16% for hKv4.3 long and 28% for hKv4.3 short compared to the maximal currents seen at +80 mV.

Figure 3A:
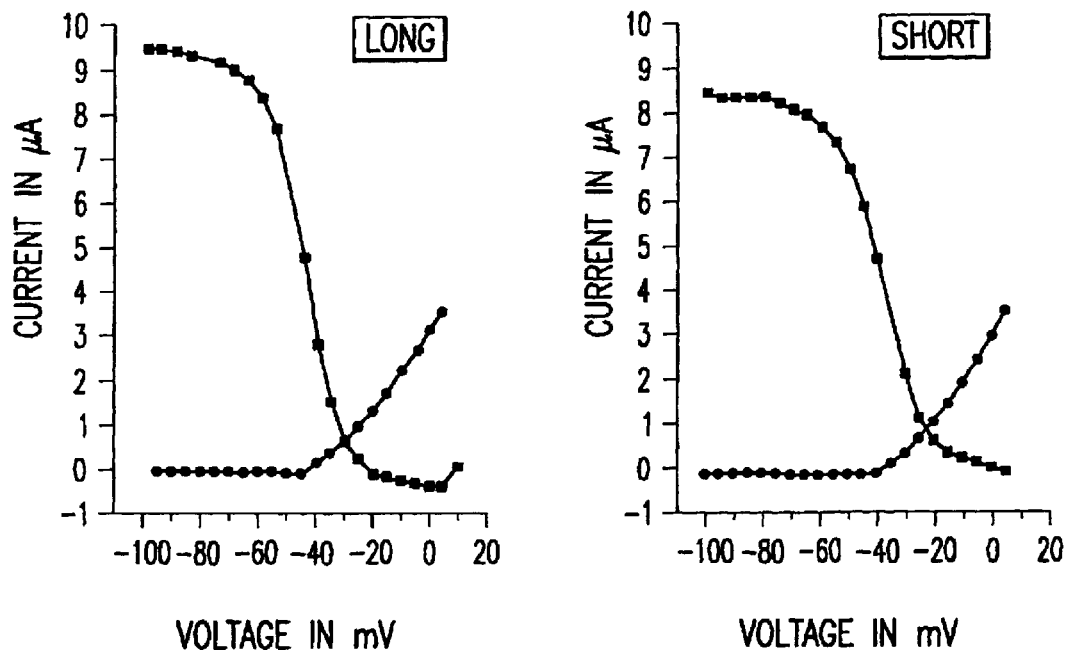
FIG. 3A. Plots of peak current for steady-state activation and inactivation of two eggs expressing short and long forms of hKv4.3.
Figure 3B:
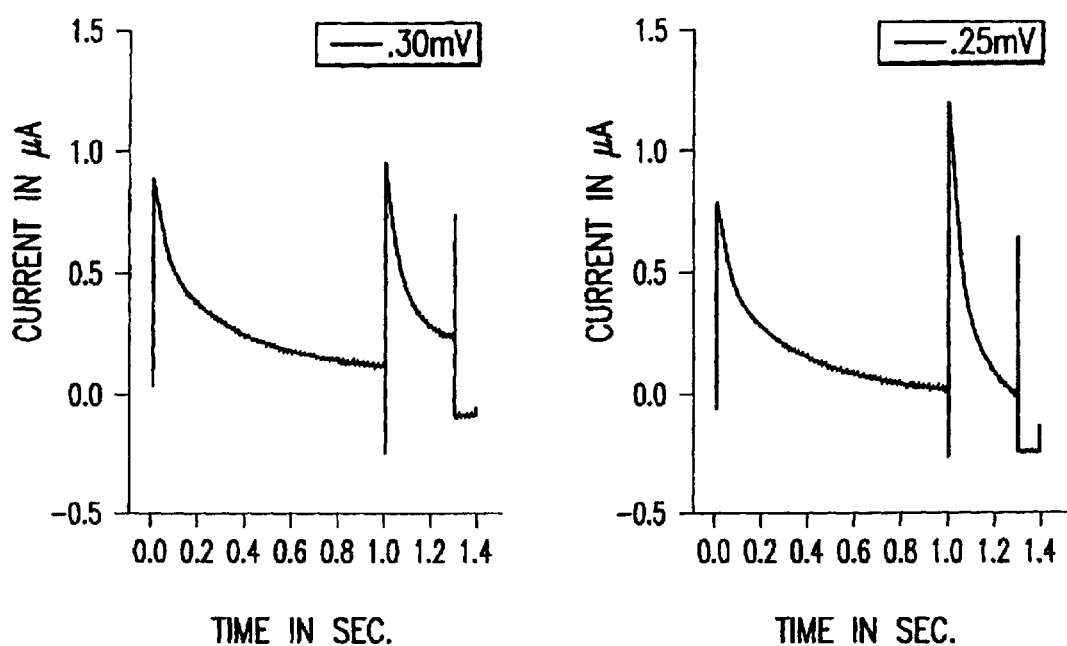
FIG. 3B. Raw current traces from the same cells in A showing partial activation and inactivation of hKv4.3 current near the peak of the window current region.
Figure 3C:
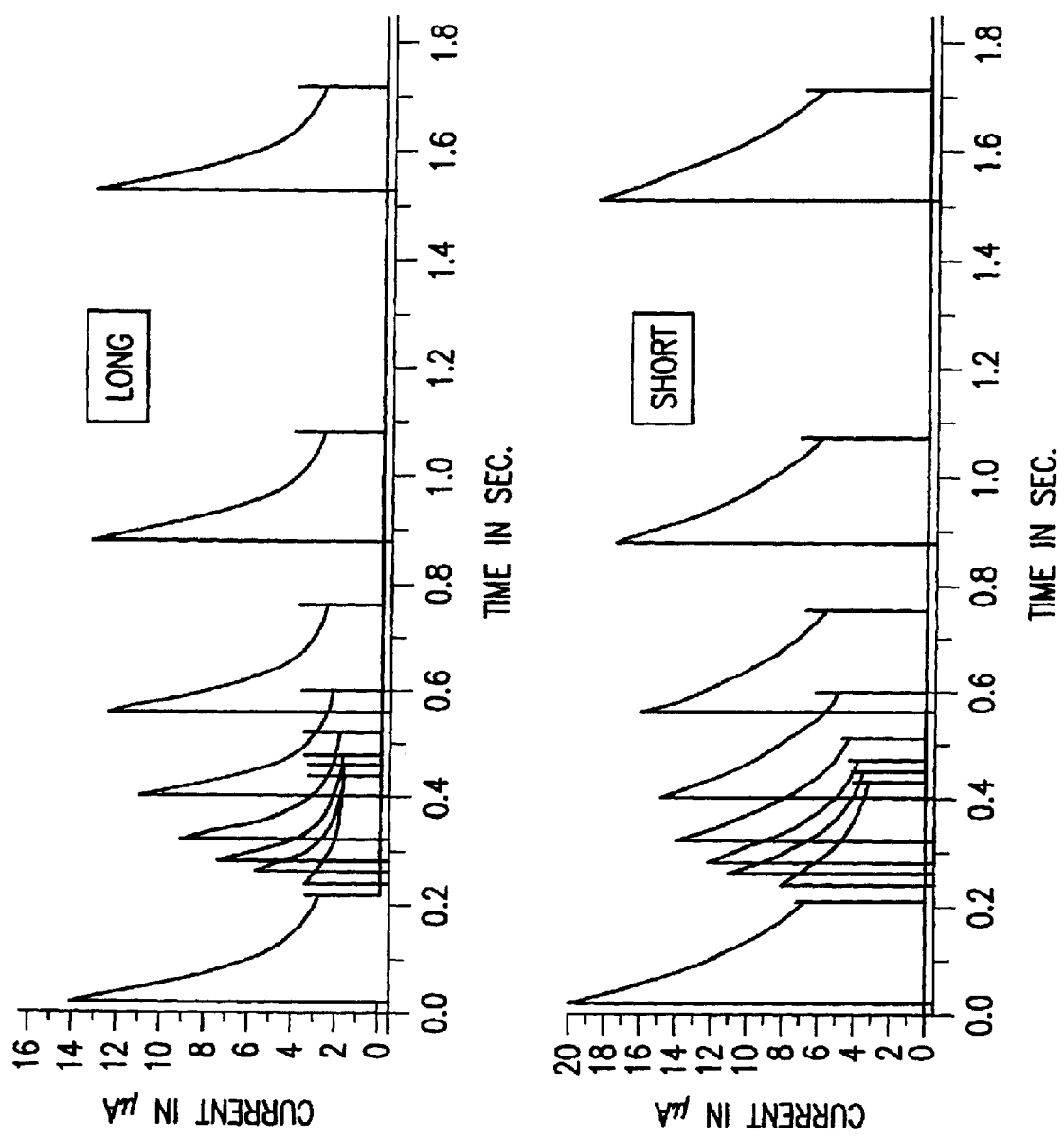
FIG. 3C. Raw current traces from both short and long forms of hKv4.3 in response to voltage steps designed to explore the recovery from inactivation. Oocyte held at −80 mV and 200 ms depolarizing voltage pulses to +60 mV delivered in pairs with the interval between them increasing.

This window current could occur at surprisingly positive potentials as demonstrated in FIGS. 3A,B which shows two individual oocytes expressing hKv4.3 short or hKv4.3 long. In the two selected cells the peak of the window current occurred at −30 (hKv4.3 long) and −22 mV (hKv4.3 short). FIG. 3C shows two different oocytes expressing both forms of hKv4.3 and the raw currents resulting from application of a voltage pulse protocol designed to look at the kinetics of the recovery from inactivation. In these two particular cells there was no difference in this recovery process. Pooled data from similar experiments on additional eggs gave a population average time constant of 356±48 ms for hKv4.3 long and 348±53 s for hKv4.3 short (n=7).

Discussion: We have cloned the human equivalent of the rat Kv4.3 channel from human brain and heart. There is a 19 amino acid region that is presumably alternatively spliced to form hKv4.3 long and hKv4.3 short. Both forms of hKv4.3 show high homology to the two rat forms that have been previously cloned with only a three amino acid difference. This high degree of amino acid conservation suggests that the Kv4.3 channel is evolutionarily highly conserved. We find from RT-PCR that both the long and short forms of the channel are expressed in the human brain but that only the long form is found in the heart. This is similar to the findings of Ohya et al. 1997 and Takimoto et al. 1997 for the two alternatively spliced forms of the rat Kv4.3 channel. The electrophysiologic data from the hKv4.3 channel are in accord with that of Serodio et al. 1996 for the short form of rat Kv4.3 in that both steady-state activation and inactivation appear to be shifted positive relative to that seen for A currents from native cells (Serodio et al. 1994 and Serodio et al. 1996). Serodio et al. (1996) fail to show saturation of the rKv4.3 current at potentials of +50 mV, although coinjection of low molecular weight RNA did shift the activation curve by 20 mV negative which allowed for complete saturation of the current at +50 mV. Our data shows that the saturating conductance for hKv4.3 alone does not occur until potentials of +80 mV (FIG. 2B).

To date no one has characterized the electrophysiologic differences between the two alternatively spliced variants of the Kv4.3 channel. The 19 amino acid insertion contains two adjacent PKC consensus sites and occurs in the carboxy domain after the sixth transmembrane domain. We find that the steady-state inactivation of hKv4.3 short is shifted 11 mV positive relative to hKv4.3 long. We also report on a prominent window current region where steady-state inactivation and activation overlap. Serodio et al. (1996) show a similar region for the short form of rKv4.3 in their study. This window current region may be of particular physiologic significance as it would provide for a sustained K conductance within the voltage range of the window current and thus provide a repolarizing influence, even for very slow membrane potential events. We did not explore the effect of low molecular weight mRNA on the voltage dependence of this window current although from Serodio et al. (1996) it would be expected to have the effect of shifting both window current voltage ranges into a subthreshold voltage range.

Hoffman et al. (1997) have recently reported on a integrating function for the A current seen on proximal and distal hippocampal neurons. In the hippocampal neurons the A current serves as a attenuator for synaptic potentials and prevents excessive retrograde propagation of action potentials triggered in the axon region. Sheng et al. (1992) and Maletic-Savatic et al. (1995) have presented evidence that the molecular correlate for the A current in hippocampal dendrites is likely to be a Kv4 channel type. If this is true then the window current region seen in our recordings of hKv4.3 channels may play a particularly significant role in damping synaptic and excitatory membrane potentials within its voltage range. For more positive potentials Kv4.3 would serve as a high frequency filter, reducing fast membrane transients but allowing slower ones through, as the inactivation kinetics of Kv4.3 would quickly inactivate the channel at these more positive potentials.

References

1. Baldwin, T. J., Tsaur, M. L., Lopez, G. A., Jan, Y. N., and Jan, L. Y. Characterization of a mammalian cDNA for an inactivating voltage-sensitive K+ channel. Neuron 7:471–483, 1991.
2. Byrne, J. H. Analysis of ionic conductance mechanisms in motor cells mediating inking behavior in Aplysia californica. J. Neurophysiol. 43:630–650, 1980.
3. Chabala, L. D., Bakry, N., and Covarrubias, M. Low molecular weight poly (A) mRNA species encode factors that modulate gating of a non-Shaker A-type K+ channel. J. Gen. Physiol. 102: 713–728, 1993.
4. Connor, J. A. and Stevens, C. F. Prediction of repetitive firing behavior from voltage clamp data on an isolated neurone soma. J. Physiol. Lond. 213:31–53, 1971b.
5. Connor, J. A. and Stevens, C. F. Voltage clamp studies of a transient outward membrane current in gastropod neural somata. J. Physiol. Lond. 213:21–30, 1971a.
6. Dixon, J. E., Shi, W., Wang, H. S., McDonald, C., Yu, H., Wymore, R. S., Chohen, I. S. and McKinnon, D. Role of the Kv4.3 K+ channel in ventricular muscle. A molecular correlate for the transient outward current. Circ. Res. 79(4), 659–668, 1996.
7. Fiset, C., Clark, R. B., Shimoni, Y., and Giles, W. R. Shal-type channels contribute to the Ca2+-independent transient outward K+ current in rat ventricle. J. Physiol. (Lond.) 500: 51–64, 1997.
8. Getting, P. A. Mechanisms of pattern generation underlying swimming in Tritonia. III. Intrinsic and synaptic mechanisms for delayed excitation. J. Neurophysiol. 49:1036–1051, 1983.
9. Hille, B. Ionic Channels of Excitable Membranes (2nd ed). Sunderland, M A: Sinauer, 1992.
10. Hoffman, D. A., Magee, J. C., Costa M. C., and Johnston, D. K+ channel regulation of signal propagation in dendrites of hippocampal pyramidal neurons. Nature. 387: 869–875, 1997.
11. Johns D. C., Nuss, H. B., and Marban, E. Suppression of neuronal and cardiac transient outward currents by viral gene transfer of dominant-negative Kv4.2 constructs. Journal of Biological Chemistry. 272(50):31598–603, 1997.
12. Llinas, R. The intrinsic electrophysiological properties of mammalian neurons: Insights into central nervous system function. Science Wash. D.C. 242:1654–1664, 1988.
13. Matetic-Savatic, M., Leen, N. J., and Trimmer, J. S. Differential spatiotemporal expression of K+ channel polypeptides in rat hippocampal neurons developing in situ and in vitro. J. Neurosci. 15:3840–51, 1995.
14. McCormick, D. A. and Huguenard, J. R. A model of the electrophysiological properties of thalamocortical relay neurons. J. Neurophysiol. 68:1384–1400, 1992.
15. Ohya, S., Tanaka, M., Oku, T., Asai, Y., Watanabe, M., Giles, W. R. and Imaizumi, Y. Molecular cloning and tissue distribution of an alternatively spliced variant of an A-type K+ channel alpha-subunit, Kv4.3 in the rat. FEBS Lett. 420 (1), 47–53, 1997.
16. Pak, M. D., Baker, K., Covarrubias, M., Butler, A., Ratcliffe, A., and Salkoff mShal, a subfamily of A-type K+ channel cloned from mammalian brain. Proc. Natl. Acad. Sci. USA 88:4386–4390, 1991.
17. Rudy, B. Diversity and ubiquity of K channels. Neuroscience 25: 729–750, 1988.
18. Serodio, P. and Rudy, B. Differential expression of Kv4 K+ channel subunits mediating subthreshold transient K+ (A-type) currents in rat brain. J. Neurophysiol. 79: 1081–1091, 1998.
19. Serodio, P., Kentros, C., and Rudy, B. Identification of molecular components of A-type channels activating at subthreshold potentials. J. Neurophysiol. 72:1516–1529, 1994.
20. Serodio, P., Vega-Saenz de Miera, E. and Rudy, B. Cloning of a novel component of A-type K+ channels operating at subthreshold potentials with unique expression in heart and brain. J. Neurophysiol. 75 (5), 2174–2179, 1996.
21. Sheng M, Tsaur M. L., Jan, J-N and Jan, Ly. Subcellular segregation of two A-type K+-channel proteins in rat central neurons. Neuron 9:271–84, 1992.
22. Takimoto, K., Li, D., Hershman, K. M., Li, P., Jackson, E. K. and Levitan, E. S. Decreased expression of Kv4.2 and novel Kv4.3 mRNAs in ventricles of renovascular hypertensive rats. Circ. Res. 81:533–539, 1997.
23. Thompson, S. H. and Aldrich, R. W. Membrane potassium channels. In: The Cell's Surface and Neuronal Function, edited by C. W. Cotman, G. Poste, and G. L. Nicholson. Amsterdam: Elsevier/North Holland, 1980, vol. 6, p. 49–85.

What is claimed is:

1. A recombinantly-produced polypeptide comprising SEQ ID NO:2.
2. A purified or chemically-synthesized polypeptide comprising SEQ ID NO:2.
3. An isolated polypeptide comprising SEQ ID NO:2.
4. A Kv4.3 potassium channel produced by expressing from a recombinant vector comprising the nucleotide sequence depicted in SEQ ID NO:1, wherein said nucleotide sequence is operatively linked to one or more expression control sequences.
5. A recombinantly-produced polypeptide comprising SEQ ID NO:4.
6. A purified or chemically-synthesized polypeptide comprising SEQ ID NO:4.
7. An isolated polypeptide comprising SEQ ID NO:4.
8. A Kv4.3 potassium channel produced by expressing from a recombinant vector comprising the nucleotide sequence depicted in SEQ ID NO:3, wherein said nucleotide sequence is operatively linked to one or more expression control sequences.

* * * * *